United States Patent [19]

Lilburn

[11] 4,259,192

[45] Mar. 31, 1981

[54] LUBRICATING OIL COMPOSITIONS CONTAINING POLYETHER DITHIOPHOSPHATES

[75] Inventor: Jennifer E. Lilburn, Berkeley, Calif.

[73] Assignee: Chevron Research Company, San Francisco, Calif.

[21] Appl. No.: 26,461

[22] Filed: Apr. 2, 1979

[51] Int. Cl.³ .......................... C10M 7/46; C07F 3/06
[52] U.S. Cl. .............................. 252/32.7 E; 260/429.9
[58] Field of Search ............................ 260/951, 429.9; 252/32.7 E

[56] References Cited

U.S. PATENT DOCUMENTS

| | | |
|---|---|---|
| 2,344,395 | 3/1944 | Cook et al. ..................... 260/951 X |
| 2,382,775 | 8/1945 | Cook et al. ............................ 260/951 |
| 3,169,923 | 2/1965 | Guarnaccio et al. ............ 260/951 X |
| 3,193,500 | 7/1965 | Hartle ................................ 260/951 X |
| 3,337,654 | 8/1967 | Cyba .,.............................. 260/951 X |
| 3,547,820 | 12/1970 | Woodward et al. ................ 252/32.5 |
| 3,791,985 | 2/1974 | Eiseman, Jr. et al. .......... 252/32.7 R |

*Primary Examiner*—Anton H. Sutto
*Attorney, Agent, or Firm*—D. A. Newell; S. R. LaPaglia; A. S. Zavell

[57] ABSTRACT

Oil-soluble dithiophosphate esters of a dithiophosphoric acid and a poly(oxyalkylene) alcohol, and salts thereof, are provided for lubricating oil compositions.

2 Claims, No Drawings

LUBRICATING OIL COMPOSITIONS CONTAINING POLYETHER DITHIOPHOSPHATES

BACKGROUND OF THE INVENTION

1. Field of the Invention

In order to reduce friction and increase the load-carrying capacity of lubricants, especially when employed under extreme-pressure conditions, additives are used which have come to be known as "EP" (extreme-pressure) agents. At high loads, these additives prevent the welding of irregularities in the two contacting surfaces which might otherwise occur, followed by metal transfer (galling) or cleavage and the production of wear fragments. A commonly used additive is a zinc dithiophosphate which is the dithiophosphate ester of dithiophosphoric acid and a hydrocarbyl alcohol. However, as the search for improved EP additives continues, alternatives to zinc dithiophosphates have been sought.

2. Description of the Prior Art

U.S. Pat. No. 3,547,820 discloses a lubricating composition containing the metal salt of a phosphate ester of an oxyalkylated hydroxy compound. U.S. Pat. No. 3,791,985 discloses a metal salt of sulfur-containing phosphate esters of alkoxylated phenols in lubricating compositions.

SUMMARY OF THE INVENTION

An oil-soluble dithiophosphate ester of a dithiophosphoric acid and a hydrocarbyl-terminated poly(oxyalkylene) alcohol, and metal salts thereof, find use as EP agents in lubricating oils. The hydrocarbyl-terminated poly(oxyalkylene) alcohol is composed of oxyalkylene units selected from 2 to 5 carbon atom oxyalkylene units, at least a sufficient number of which are branched-chain oxyalkylene units to render said dithiophosphate ester soluble in an oil of lubricating viscosity. Said hydrocarbyl group contains from 1 to about 30 carbon atoms.

DESCRIPTION OF PREFERRED EMBODIMENTS

Dithiophosphate

The dithiophosphate of the present invention is a diester of dithiophosphoric acid and a hydrocarbyl-terminated poly(oxyalkylene) alcohol. The dithiophosphate is preferably of molecular weight from about 500 to 5000. Salts of the dithiophosphates are also included within the scope of this invention, in particular, dithiophosphate salts of alkali, alkaline earth and heavy metals, but including ammonium salts. The dithiophosphates may be used as lubricating additives in their free-acid form or in the form of their salts such as sodium, potassium, calcium, magnesium and barium salts. Of these, the heavy metal salts, i.e., iron, zinc, lead, cadmium and copper are the preferred EP agents, as are the ammonium salts and substituted ammonium (amine) salts, e.g., methylamine, propylamine, mono-, di-, and trimethanolamine salts. The most preferred EP agents within the scope of this invention are the zinc salts.

The dithiophosphates are made by the reaction of the alcohol with phosphorus pentasulfide ($P_2S_5$) to produce the freeacid dithiophosphate. The latter may be further reacted with a base to provide the aforementiond salt, e.g., dithiophosphate is reacted with zinc oxide to produce the zinc dithiophosphate.

Hdrocarbyl Poly(oxyalkene) Alcohol

The hydrocarbyl-terminated poly(oxyalkylene) polymers which are utilized in preparing the dithiophosphates of the present invention are monohydroxy compounds, i.e., alcohols, often termed monohydroxy polyethers, or "capped" poly(oxyalkylene) glycols and are to be distinguished from the poly(oxyalkylene) glycols (diols), or polyols, which are not hydrocarbyl-terminated, i.e., not capped. The hydrocarbyl-terminated poly(oxyalkylene) alcohols are produced by the addition of lower alkylene oxides, such as oxirane, ethylene oxide, propylene oxide, the butylene oxides, or the pentylene oxides to the hydroxy compound ROH under polymerization conditions. Methods of production and properties of these polymers are disclosed in U.S. Pat. Nos. 2,841,479 and 2,782,240, and the aforementioned Kirk-Othmer's "Encyclopedia of Chemical Technology", Volume 19, p. 507. In the polymerization reaction a single type of alkylene oxide may be employed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxide is copolymerized with other oxides, the higher reaction rate of ethylene oxide makes the preparation of random copolymers difficult. In either case, block copolymers can be prepared. Block copolymers are prepared by contacting the hydroxyl-containing compound with first one alkylene oxide, then the others in any order, or repetitively, under polymerization conditions. A particular block copolymer is represented by a polymer prepared by polymerizing propylene oxide on a suitable monohydroxy compound to form a poly(oxypropylene) alcohol and then polymerizing butylene oxide on the poly(oxypropylene) alcohol.

In general, the poly(oxyalkylene) polymers are mixtures of compounds that differ in polymer chain length. However, their properties closely approximate those of the polymer represented by the average composition and molecular weight.

The hydrocarbylpoly(oxyalkylene) moiety of the dithiophosphate consists of two hydrocarbyl-terminated poly(oxyalkylene) polymers composed of oxyalkylene units containing from 2 to about 5 carbon atoms. The hydrocarbyl group contains from 1 to about 30 carbon atoms, preferably from 2 to about 20 carbon atoms. Preferably the oxyalkylene units contain from 3 to 4 carbon atoms and the molecular weight of the hydro-carbylpoly(oxyalkylene) moiety is from about 200 to about 10,000, more preferably from about 500 to about 5,000. Each poly(oxyalkylene) moiety contains at least one oxyalkylene unit, preferably 8 to about 100 oxyalkylene units, more preferably about 10-100 units and most preferably 10 to about 25 such units. The higher oxyalkylene polymers are generally, within the limits of oil solubility, preferred for their lubricant properties. In general, the oxyalkylene units may be branched or unbranched. Preferably the poly(oxyalkylene) polymer chain contains at least some $C_3$-$C_5$ oxyalkylene units, more preferably, branched $C_3$-$C_5$ oxyalkylene units are present in at least sufficient number to render the hydrocarbyl-terminated poly(oxyalkylene) dithiophosphate soluble in the lubricating oil composition of the present invention. This solubility condition is satisfied if the dithiophosphate is soluble in hydrocarbons of lubricating viscosity, i.e., about 35–50,000 SUS, at 38° C., at least to the extent of about 0.01 percent by weight. A poly(oxyalkylene) polymer chain composed of branched three and/or four carbon oxyalkylene units in at least sufficient amount to effect solubility in the lubricating oil composition is most preferred. The structures of the $C_3$-$C_5$ oxyalkylene units are any of the isomeric structures well known to the organic chemist, e.g., n-propylene, —$CH_2CH_2CH_2$—; isopropylene; —$HC(CH_3)CH_2$—; n-butylene, —$CH_2CH_2CH_2CH_2$—; sec.-butylene, —$CH(CH_2CH_3)CH_2$—; tert.-butylene, $C(CH_3)_2CH_2$—; disec.-butylene, —$CH(CH_3)CH(CH_3)$—; isobutylene, —$CH_2CH(CH_3)CH_2$—; etc. The preferred poly(oxyalkylene) compounds are composed, at least in part, of the branched oxyalkylene isomers, particularly oxy(isopropylene), and oxy(sec.-butylene) units which are obtained from 1,2-propylene oxide and from 1,2-butylene oxide, respectively. The inclusion of at least one $C_{11}$-$C_{30}$ epoxide unit in the poly(oxyalkylene) chain provides a branched-chain and is a preferred method of assisting solubility in this invention.

The hydrocarbyl moiety (R) which terminates the poly(oxyalkylene) chain contains from 1 to about 30 carbon atoms, preferably from 2 to about 20 carbon atoms, and is generally derived from the monohydroxy compound (ROH) which is the initial site of the alkylene oxide addition in the polymerization reaction. Such monohydroxy compounds are preferably aliphatic or aromatic alcohols of from 1 to about 30 carbon atoms, more preferably an alkanol or an alkylphenol, and most preferably an alkylphenol wherein the alkyl is a straight or branched chain of from 1 to about 24 carbon atoms. One such preferred alkyl group is obtained by polymerizing propylene to an average of 4 units and has the common name of propylene tetramer. The preferred material may be termed either an alkylphenylpoly(oxyalkylene) alcohol or a polyalkoxylated alkylphenol.

Suitable lubricating oils which can be used to prepare a lubricating oil composition or concentrate of this invention are oils of lubricating viscosity derived from petroleum or synthetic sources. The oils can be paraffinic, napthenic, halo-substituted hydrocarbons, synthetic esters, polyethers, alkylbenzenes, or combinations thereof. Oils of lubricating viscosity have viscosities in the range of 35 to 50,000 SUS at 38° C., and more usually from about 50 to 10,000 SUS at 38° C. The amount of the dithiophosphate of this invention which is incorporated into the lubricating oil to provide the effective amount necessary for dispersancy varies widely with the particular dithiophosphate used as well as the use intended for the lubricating oil composition. Other conventional additives which can be used in combination with the poly(oxyalkylene) dithiophosphate of this invention include ashless dispersants such as the type disclosed in U.S. Pat. Nos. 3,172,892, 3,219,666, 3,381,022; neutral and basic calcium, barium and magnesium petrosulfonates or alkylphenates; oxidation inhibitors, antifoam agents, viscosity index improvers, pour-point depressants, and the like, such as chlorinated wax, benzyldisulfide, sulfurized sperm oil, sulfurized terpene; phosphorus esters such as trihydrocarbon phosphites and phosphates; polyisobutene having an average molecular weight of 100,000; etc.

In general, the lubricating oil compositions will contain from about 0.01 to about 20 weight percent of said oil-soluble dithiophosphate. More usually, the lubricating oil composition of the invention will contain from about 0.5 to about 10 weight percent of the dithiophosphate and more usually from about 1 to about 8 weight percent of the dithiophosphate.

In a second embodiment of this invention, lubricating oil additive concentrates are provided comprising from about 90 to about 20 weight percent of an inert stable oleophilic solvent such as oil of lubricating viscosity and from about 10 to about 80 weight percent of the poly(oxyalkylene) dithiophosphates of this invention. Typically, the concentrates contain sufficient diluent to make them easy to handle during shipping and storage. Preferably, the diluent is an oil of lubricating viscosity so that the concentrate may be readily mixed with lubricating oils to prepare lubricating oil compositions. Suitable lubricating oils which can be used as diluents typically have viscosities in the range from about 35 to about 1000 Saybolt Universal Seconds (SUS) at 38° C. although any oil of lubricating viscosity can be used.

EXEMPLIFICATION

The following examples are presented to illustrate specific embodiments of the practice of this invention and should not be interpreted as limitations upon the scope of the invention.

Example 1—Preparation of Alkylphenylpoly(oxybutylene)

The experiment was carried out under inert atmosphere in dry glassware. 52.69 g (0.2 mol) of a phenol alkylated with propylene tetramer was placed in a 2-liter, 3-necked flask. 2.61 g (0.067 mol) of clean potassium was added to the flask using a positive nitrogen pressure in the system. The mixture was stirred and heated to 100° C. for a period of 20 hours, until the potassium dissolved in the phenol. The freshly distilled 1,2-epoxybutane, 172 ml (2.0 mols) was added at a temperature of 180° C. via a dropping funnel at such a rate as not to flood the condenser. After addition of the epoxybutane, the pot temperature dropped to 64° C. Stirring and heating were continued for 21 hours until the pot temperature reached 117° C. To the reaction flask was added 180 ml of Bio-Rad AG 50W-X2 resin and the mixture stirred for 2 hours at 70° C., filtered, stripped on a rotary evaporator and azeotroped with toluene. Yield: 176.8 g.

Example 2—Preparation of Alkylphenylpoly(oxybutylene) Dithiophosphate

To a 500-ml, 3-necked flask containing 9.0 g (0.04 mol) of $P_2S_5$ and 150 ml of dry toluene, was attached a KOH trap to contain any $H_2S$ which would be evolved during the reaction. 125 g (0.163 mol) of the product of Example 1 was added dropwise to the reaction mixture. No exotherm was noted during the addition. The reaction mixture was heated to reflux and stirred overnight. The product was filtered through diatomaceous earth (Celite 545), stripped and azeotroped on the rotary evaporator. Yield: 134 g. The material contained 1.85 weight percent P, 3.10 percent S and had an average molecular weight of 1350.

Example 3—Preparation of Zinc Dithiophosphate of Alkylphenylpoly(oxybutylene)

12.5 g of the product of Example 2, 3.75 g of zinc oxide and 100 ml of dry toluene were placed in a 3-necked flask. The mixture was heated and stirred to 70° C. when an additional 37.5 g (0.061 mol total) of the dithiophosphoric acid was added dropwise via a dropping funnel. The mixture was stirred at 70° C. for 4 hours, whereupon the pH was found to be 7. The product was filtered and stripped on a rotary evaporator and azeotroped with toluene. Yield: 37 g. The material contained 1 58 weight percent P, 1.86 percent Zn, and 3.05 percent S.

EVALUATION

The alkylphenylpoly(oxyalkylene) dithiophosphate of Example 3 was tested in Falex EP and 4-Ball Wear Tests against two alkyldithiophosphates. All three additives were tested at about 36 mmols of phosphorus per kilogram of oil (about 18 mmols of zinc per kilogram of oil) in an otherwise unadditized neutral oil of lubricating viscosity. The results, shown in the following two tables, indicate that the alkylphenylpoly(oxyalkylene) dithiophosphate provides lubricity, and performs at least as well and usually better than other dithiophosphates in extreme-pressure tests.

TABLE I

| Additive | 4-Ball Wear Test[1] | | |
|---|---|---|---|
| | % in Cit-Con 100N | mmol P/ kg oil | Scar Diameter, mm |
| None | — | 0 | 1.97 |
| Example 3 | 6.1 | ca. 36 | 0.64 |
| Alkyl dithiophosphate[2] | 1.25 | 36 | 0.72 |
| Aryl dithiophosphate[3] | 3.5 | 36 | 1.01 |

[1]40-kg load, 54° C., 1800 rpm, 60 min., steel
[2]zinc dioctyl dithiophosphate
[3]zinc bis(polypropylenephenyl) dithiophosphate.

TABLE II

| Additive | Falex EP Test | | |
|---|---|---|---|
| | % in Cit-Con 100N | First Seizure Load, lb | Second Seizure Load, lb |
| None | — | 850 | 800 |
| Example 3 | 6.1 | 1250 | 1400 |
| Alkyl dithiophosphate[1] | 1.25 | 800 | 825 |
| Aryl dithiophosphate[2] | 3.5 | 1175 | 1150 |

[1]See footnote 2, Table I
[2]See footnote 3, Table I

What is claimed is:

1. A lubricating oil composition comprising a major amount of an oil of lubricating viscosity derived from petroleum sources and a minor amount of the zinc salt of a dithiophosphate ester of a dithiophosphoric acid and a hydrocarbyl-terminated poly(oxyalkylene) alcohol, wherein said hydrocarbyl-terminated poly(oxyalkylene) alcohol is of molecular weight of from about 200 to 10,000 and is composed of about 8–100 oxyalkylene units selected from 3 to 5 carbon atom oxyalkylene units, at least a sufficient number of which are branched-chain oxyalkylene units to render said zinc salt soluble in an oil of lubricating viscosity, and said hydrocarbyl group contains from 1 to 30 carbon atoms.

2. A concentrate comprising an inert stable oleophilic organic solvent and from 10 to 80 weight percent of the composition of claim 1.

* * * * *